United States Patent [19]

Ecer

[11] Patent Number: 5,412,564
[45] Date of Patent: May 2, 1995

[54] SYSTEM AND METHOD FOR DIET CONTROL

[76] Inventor: Gunes M. Ecer, P.O. Box 4025, Thousand Oaks, Calif. 91359

[21] Appl. No.: 191,947

[22] Filed: Feb. 3, 1994

[51] Int. Cl.$^6$ .................................... G06F 19/00
[52] U.S. Cl. ................................... 364/413.29
[58] Field of Search ............... 364/413.02, 413.29; 235/380

[56] References Cited

U.S. PATENT DOCUMENTS

| | | | |
|---|---|---|---|
| 4,321,674 | 3/1982 | Krames et al. | 364/413.29 |
| 4,686,624 | 8/1987 | Blum et al. | 364/413.29 |
| 4,891,756 | 1/1990 | Williams, III | 364/413.29 |
| 5,006,699 | 7/1991 | Felkner et al. | 235/472 |
| 5,047,614 | 11/1991 | Bianco | 235/385 |
| 5,111,030 | 5/1992 | Brasington et al. | 235/375 |
| 5,120,945 | 6/1992 | Kunihiko et al. | 235/379 |
| 5,159,183 | 10/1992 | Yamaguchi | 235/380 |
| 5,233,520 | 8/1993 | Kretsch et al. | 364/413.29 |

*Primary Examiner*—F. L. Evans
*Attorney, Agent, or Firm*—William W. Haefliger

[57] ABSTRACT

A system and a method for recording and monitoring of dietary consumption by a consumer is disclosed. The system consists of a computer for storing and processing nutritional information of the type used for diet control, a real time clock for maintaining current date record, a product code entry terminal or a bar code reader for inputting product identification information, a read-write unit adapted to receive one or more integrated circuit (IC) cards of the smart card type having memory and a microprocessor for reading and writing nutritional information into and from a smart card, a printer for printing nutritional information, and optionally an electric display for displaying such information. Consumer inserts his/her personalized smart card into card reader writer before a purchase transaction starts at a food store or a restaurant check-out counter. As foods and drinks are purchased, dietary nutritional consumption data is electronically collected, sorted, and combined with historical daily averages of nutritional consumption data stored in consumer's personalized smart card and daily averages of nutrition consumption along with other nutritional and personal data is printed out as a report to the consumer at the end of the purchase transaction. Nutritional data may include personal consumption data on calories, calories from fat, calories from sugars, and cholesterol, dietary fibers, sodium, carbohydrates, proteins, and the like. Consumer's smart card serves as a personal nutritional consumption history file, and is updated each time it is used.

5 Claims, 3 Drawing Sheets

Dietary Consumption Report for John Doe Fit & Family

Total Family Members: 5
Card Activation Date: June 1, 1993
Report Date: Jan. 15, 1994

| Nutrient Type | Average Daily Consumption Per Person | | Amount Per Person Last Purchase |
|---|---|---|---|
| | To Date | Last 30 Days | |
| Calories | 2890 | 2827 | 8595 |
| --From Fat, % | 39 | 36 | 32 |
| --From Sugars, % | 17 | 16 | 21 |
| Protein, g | 145 | 139 | 434 |
| Cholesterol, mg | 413 | 361 | 882 |
| Sodium, mg | 4901 | 4107 | 9822 |
| Dietary Fiber, g | 12 | 19 | 64 |

Dietary Consumption Report for Jane Doe

Total Family Members: 1
Card Activation Date: June 1, 1993
Report Date: Jan. 15, 1994

| Nutrient | Recommended Daily Amount | Average Daily Consumption/Person | | Amount/Person Last Purchase |
|---|---|---|---|---|
| | | To Date | Last 30 Days | |
| Calories | 2000 max | 2523 | 2214 | 7995 |
| ---From Fat | 600 max | 944 | 821 | 2206 |
| ---From Sugars | -- | 450 | 404 | 1346 |
| Protein, g | -- | 195 | 149 | 422 |
| Cholesterol, mg | 300 max | 416 | 301 | 748 |
| Sodium, mg | 2500 max | 5231 | 4204 | 8522 |
| Dietary Fiber, g | -- | 22 | 19 | 64 |

Summary Dietary Report
Date: January 15, 1994

| Nutrient Type | Amount (%) in This Purchase |
|---|---|
| Calories | 7995 (100) |
| Calories From Fat | 2206 (28) |
| Calories From Sugars | 1346 (17) |
| Calories from complex carbohydrates | 3802 (48) |
| Protein, g | 422 |
| Cholesterol, mg | 748 |
| Sodium, mg | 8522 |
| Dietary fiber, g | 64 |

FIG.5

SYSTEM AND METHOD FOR DIET CONTROL

BACKGROUND OF THE INVENTION

1. Field of Invention

This invention relates to diet control. More specifically, to a system and a method of electronically collecting and recording personalized nutritional consumption data of the type of concern in diet control when foods and drinks are purchased at food store check-out counters.

2. Description of the Prior Art

The word diet has two most commonly used definitions related to foods. First, it is the usual food or drink of a person or an animal. Second, it is a regulated selection of foods, especially as prescribed for gaining or loosing weight or for other medical reasons. During the last several years, the process of dieting to loose weight is being discovered to be the most ineffective and needlessly expensive of all human experiences. After depravation and discipline for days, weeks, and even months to achieve a goal, dieters are often seen gaining back all that they lost within a short period of time. Many dieters put themselves through this process regularly. Each time quickly returning where they had started, and each time trying a new diet cure available on the market. Invariably, the cost of this perpetual circle of disappointment is more than just monetary. Many times their real cost is a person's mental and physical health.

In most cases, the remedy offered by a "fad" diet is depravation. This is why most diets do not work. A person deprived of food for the duration of the diet naturally thinks of eating when it is finally over. The answer to weight control lies in having the right diet, the right amount of exercise, focusing on fat (not weight), and never going hungry (without deprivation).

There is no ideal diet that could possibly meet the varying food needs of a population that has so many different ages, body sizes, physical activities, and health problems. However, practical guidelines based on scientific research are offered by the United States Departments of Agriculture and Health and Human Services. These guidelines are accepted by the mainstream medical community as sound advice for good nutrition. These are: (1) eat a variety of foods. (2) Eat foods high in starch and fiber. (3) Avoid too much fat, saturated fat and cholesterol. (4) Reduce sugar intake. (5) Reduce salt intake. (6) Maintain ideal weight. (7) If you drink alcohol, do so in moderation.

Eating right is important not just for weight control, but also for maintaining a healthy body. Increasingly, research is showing that diet affects how likely one is to develop certain diseases. Along with smoking and high blood pressure, high levels of cholesterol in the blood has been accepted as a major risk factor for heart disease. Eating too much rich, fat food increases the incidence of cardiovascular disease, cancer, and diseases associated with obesity (including diabetes, gout, osteoarthritis, gallbladder disease and high blood pressure).

It is clear that a healthy diet should emphasize real, wholesome, and unprocessed foods. These are the foods that are generally high in nutrients and dietary fiber and low in sugar, salt, fat, and cholesterol. The best way to assure a healthy diet is to keep overall fat, sugar, salt, and cholesterol content of foods and drinks purchased below certain levels, and to keep such beneficial foods as dietary fibers, carbohydrates, and iron-rich foods above certain levels. However, this is a very difficult and time consuming task. It requires a knowledge of the nutritional content of items being purchased and an ability to quickly create per capita daily averages for selected nutrients for pre-selected time periods such as latest purchase, latest week, and year to date. No prior art provides such data, simply because it is a very time consuming process to keep such records. On the other hand, the question remains: how does one know if he or she is following a low fat, low cholesterol diet, or is missing out on some beneficial nutrients? Similarly, how can a diabetic person know of his/her total or average daily sugar intake from the foods he/she consumes?

This invention provides a simple and effective answer to the above questions. The system provided requires little or no time expenditure on the pan of the consumer. Nutritional data are provided electronically and automatically to the consumer at check-out counters when foods and drinks are purchased. Moreover, each family or individual can be provided with nutritional data automatically averaged over selected time periods such as latest purchase, latest week, latest month, and year to date, etc.

OBJECTS AND SUMMARY OF THE INVENTION

It is one object of the present invention to provide a convenient system of recording and monitoring of nutritional data of the type of concern in diet control at the time of purchase of foods and drinks.

It is another object of the present invention to provide a system for electronically and automatically creating a record of selected nutritional data of the type of concern in diet control on foods and drinks purchased for consumption.

It is another object of the present invention to provide a method for electronically and automatically creating a record of nutritional data of the type of concern in diet control on foods and drinks purchased for consumption.

Still another object of this invention is to provide a system for electronically and automatically creating a record of nutritional data of the type of concern in diet control averaged over preselected periods of time on foods and drinks purchased for consumption.

Still another object of this invention is to provide a method for electronically and automatically creating a record of nutritional data of the type of concern in diet control averaged over preselected periods of time on foods and drinks purchased for consumption.

To accomplish these objectives, this invention provides a system and a method associated with the use of the system, by which average per capita nutritional consumption data is automatically computed at a check-out counter, sorted, collated, processed and stored in a personalized integrated circuit (IC) card of the smart card type when purchasing foods and drinks for personal consumption. Average per capita nutritional consumption data may include calories, calories from fat, calories from sugars, and cholesterol, dietary fibers, sodium, carbohydrates, proteins, and the like expressed in terms of weight or weight percent of a desired level or maximum limit. The check-out counter may be in a supermarket, restaurant, or any other place that sells foods and drinks for human consumption. The system consists of means such as a computer for storing and processing nutritional information of the type used for diet control, means such as a real time clock for maintaining current date record, means such as a product code entry terminal or a bar code reader for inputting product identification information, means such as a read-write unit adapted to receive one or more smart cards having memory and a microprocessor for reading and writing nutritional information into and from a smart card, means such as a printer for printing nutritional information, and optionally means for displaying such information.

In the preferred embodiment, the computer has a memory in which the diet related nutritional data on all types and brands of foods and drinks and their product identification codes are stored. The bar code reader decodes the product code affixed on the food item being purchased, and transmits the information to the computer. Product code may also be entered manually via a terminal. The computer, upon receiving the product identification transmission, finds the nutritional data on the identified product stored in its memory, and sorts, collates and adds the data to those of the other food items in the same purchase, and calculates nutritional totals. When the purchase is completed, the computer communicates with the card read-write unit in which the consumer's personalized smart card is inserted, receives from the smart card information on the historical average daily consumption of dietary nutrients and the date of activation of the card. New daily averages are then calculated by the computer by combining the historical data received from the card with the data from the last purchase stored in the card's memory. Computer orders the read write unit to erase historical daily consumption averages and last purchase data from the memory of the smart card and to write the new historical daily consumption averages and the new latest purchase data in the smart card's memory for storage until the next purchase. The computer then prints the new data or displays them or does both.

Average daily consumption of nutrients may be organized as a table, and printed to provide data on the latest purchase, on the latest month's purchases, and on the purchases from the beginning to date. Several different nutritional data categories of importance to the consumers concerned about their nutritional intake such as total calories per day, calories from fat, calories from sugars, milligrams (mg) of cholesterol per day, milligrams of sodium per day, grams of dietary fiber per day, grams of protein per day, etc., are included in the table. Such tables can conveniently be printed at the end of check-out counter receipts which ordinarily lists only the items purchased, and their weights and costs. This way, consumers would have a direct knowledge of their nutritional consumption, and be able to monitor the effectiveness of their attempts to control their dietary habits. Additionally, consumers would be able to keep the daily consumption of certain nutritional items, such as sodium, cholesterol, and fat below limits as required by their physicians.

Consumers, by shopping only at those stores and restaurants that are equipped with the above described system, would be able to account for a substantial portion of their food and drink consumption. The computer may be programmed to calculate average per capita daily consumption of dietary nutrients for families. For example, a mother who shops for her family of four may be issued a smart card that informs the computer that the assignee of the card shops for a family of four. The computer then divides all daily nutritional averages by four, except those that are expressed as percentages.

In addition, it is contemplated that the system in its simplest form may consist of means such as a computer for storing and processing nutritional information of the type used in diet control, means such as a real time clock for maintaining current date record, means such as a product code entry terminal or a bar code reader for inputting product identification information, and means such as a printer for printing nutritional information, and optionally means for displaying such information. This simple form of the system is capable of informing the consumer of the nutritional content of his/her purchases at the check-out counter, but does not allow historical nutritional consumption data to be conveniently developed and stored in a personalized smart card assigned to individuals or families. To monitor progress of his/her diet control efforts, consumer in this simplest form of the invention must collect printed food store check-out reports, chronologically sort them, and analyze the nutritional consumption trends personally. While this method of diet control may be less convenient and open to errors, it is also less costly since the costs associated with purchase and distribution of smart cards to consumers, installation of card reader writer devices at food and drink selling stores and restaurants would be eliminated.

The company or the organization, issuing the personalized smart card, has the freedom to program individual preferences into the smart card. For example, daily nutritional consumption averages may be computed as a percentage of a pre-selected daily value or a maximum recommended by the individual consumer's physician, or consumer's preferences (goals) may simply be shown as a comparison. Cholesterol, sugar, and sodium are among those nutritional items that may be limited to a maximum daily average consumption by a physician for some persons. The physician imposed limits, written in the memory of the personalized smart card prior to its issuance to the consumer, may then be used in computation of the "percent of daily allowed values" by the computer or simply listed in the dietary report as a comparison. Such limits may not be the same for everyone and may change with time. Thus, periodically consumers may be provided with updated smart cards reflecting more up to date consumers' preferences which, in some cases, may be shaped by instructions from their physicians.

Advantageously, since many of the food markets and supermarkets already have in their check out systems, bar code readers, terminals for manual entry of product codes, printers that print receipts, and a computer with memory that stores product related information such as cost, size and manufacturer, it would be possible to simply retrofit the smart card read write units and smart cards forming part of the present invention to existing electronic check-out counter systems in a known manner through a communications link, and the existing food store check-out software may be modified within the skill in the art to include nutritional data of the type used for diet control, and the computer be enabled to interact with the card read write unit, and be enabled to compute daily nutritional consumption averages and/or percent daily consumption values.

Thus, there is disclosed herein a system and a method for recording and monitoring of individualized consumption of dietary nutrients of the type used in diet control. It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate principles and preferred embodiments of the present invention, and together with the description serve to explain the principles of the invention, in which:

FIG. 5 is an example of a non-personal summary dietary report, in accordance with the second embodiment of the invention, without historical dietary consumption data.

DETAILED DESCRIPTION OF THE PREFERRED EMBODIMENTS

Figures 1, 2:
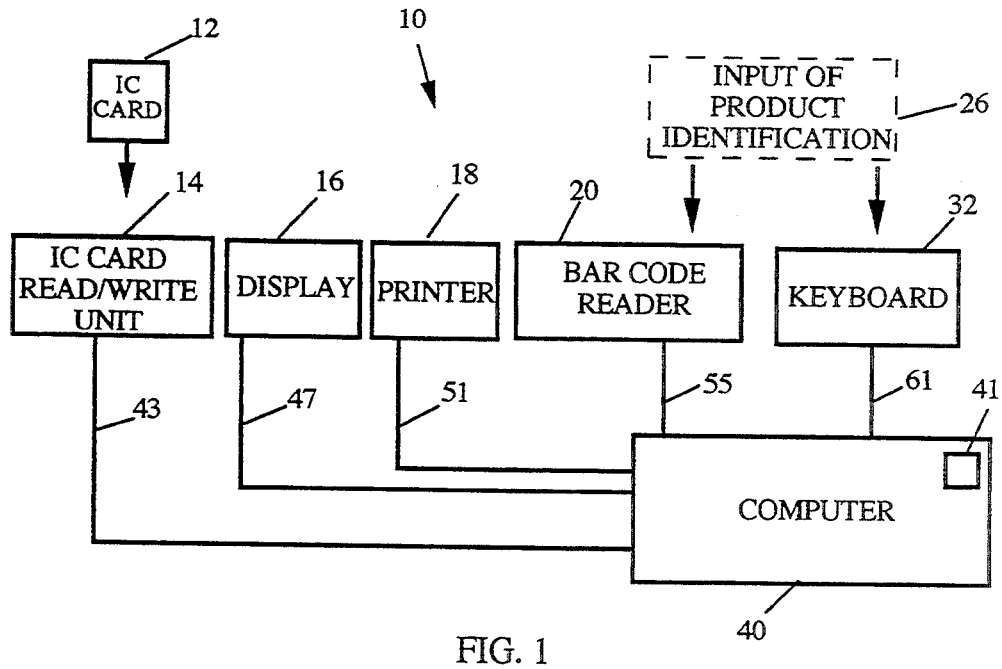
FIG. 1 is a block diagram of the personalized dietary nutritional consumption data recording and monitoring system in accordance with one embodiment of the invention.
FIG. 2 is a first example of a personalized dietary consumption report.

Referring now to the drawings, them is shown in block diagram form in FIG. 1 one example of a nutritional consumption data recording and monitoring system 10, in accordance with the preferred embodiment of the invention, by which selected nutritional data is automatically collected at a check-out counter, sorted, collated, processed, and stored in a personalized integrated circuit (IC) card of the smart card type when purchasing foods and drinks for personal consumption. Smart cards, as utilized in this invention, are personalized to the specific needs of an individual or a family, or a group of individuals. The check-out counter may be in a supermarket, restaurant, or any other place that sells foods and drinks for human consumption.

The system 10 consists of means such as a computer 40 for storing and processing nutritional information of the type of concern in diet control for all types, sizes, and brands of foods organized against their respective product identification codes or brand names, means such as a real time clock 41 incorporated into computer 40 for maintaining current date record, means such as a product code entry terminal 32 connected to computer 40 in a known manner through a communication link 61 or a bar code reader 20 connected to computer 40 in a known manner through a communication link 55 for inputting product identification information, means such as a read-write unit 14 adapted to receive one or more smart cards 12 with memory and a microprocessor for reading and writing nutritional information from and into a smart card, printing means such as a printer 18 which is in communication with computer 40 in a known manner through a communication link 51, printer 18 being at least in part used for printing nutritional consumption information of the type used in diet control, and optionally, means such as a liquid crystal display 16 which is connected in a known manner by a communications link 47 to computer 40 for displaying nutritional information. Computer 40 is provided with an appropriate program within the skill in the art enabling the computer to interact with the card read write unit 14 which is connected to computer 40 in a known manner by a communications link 43. It is contemplated that display 16 and printer 18 may be placed within close proximity and communicate with the computer 40 through the same communications link 51 or 47.

Computer 40 is further provided with an appropriate program within the skill in the art enabling computer 40 to compute daily average consumptions of nutrients of the type used in diet control and organize the data as a table, and at the end of the purchase transaction transmit the table to both printer 18 for printing and to smart card 12 for storage for future use. During the purchase transaction, nutritional contents of individual food or drink items being scanned by bar code reader 20 or being entered through keyboard terminal 32 may be displayed briefly at display 16 and foods and drinks too rich in certain unwanted nutrients such as fat and cholesterol may be conveniently highlighted as a warning to the consumer that a product too rich in the unwanted nutrient has been purchased. When the end of the purchase transaction is reached, a summary table of the nutritional content of the total purchase may optionally be displayed at display 16.

In practice, a number of smart cards 12 designed to be used with read write unit 14 are distributed to consumers interested in monitoring their diets. Consumers are asked to carry the smart cards in their person so that they can be used every time food or drink purchases are made. An example for the smart card 12 suitable for use in the present invention is the Scot 50 card containing an electronically era-sable programmable memory (EE-PROM) and security features that may be requested by consumers in order to protect personalized dietary information stored in the card. Scot 50 may be obtained from Bull CP8, Louveciennes, France, and from Micro Card Technologies Inc., Vienna, Va. A reader writer unit 14 compatible with the Scot 50 is the TLP 20,24 NV smart card reader writer available from the same companies. The TLP 224 NV uses an RS 232-C asynchronous link to a computer equipped with an RS 232-C serial port. Food stores such as supermarkets, restaurants, and the like, where foods and drinks for human consumption are sold, are provided with the system 10 shown in FIG. 1 excluding the smart cards 12. At the food store check-out counters, consumer inserts his/her personalized smart card 12 into read write unit 14 transmitting a signal to computer 40 indicating smart card's readiness to accept information. When foods and drinks being purchased by the consumer are checked-out at the check-out counter, either bar code reader 20 or keyboard terminal 32 is used to enter product identification code 26 into computer 40. Bar code reader 20 includes a bar code scanner and a decoder that transforms the electrical signal from the scanner into ASCII (American Standard Code for Information Interchange) representations of product identification code and product type which are received by computer 40 in a known manner by a communications link 55. American grocery industry uses the Universal Product Code (UPC) as the bar code symbology on their products. UPC is a subset of the more general EAN code wherein the country of origin of the product is encoded into the bar code. Scanners equipped to read EAN symbols can read UPC symbols as well, while reverse may not necessarily hold.

Computer 40, upon receiving the product identification signal from either bar code reader 20 or terminal 32, finds the nutritional data on the identified product stored in its memory and transfers them to a temporary memory location, sorts, collates and adds the data to those of the other food items in the same purchase and calculates nutritional totals. When the (current) purchase is completed, computer 40 communicates with card read-write unit 14 in which the consumer's personalized smart card 12 is inserted, asks for and receives from the smart card information on the (historical) daily averages of the selected nutritional consumption data calculated on prior purchases, number of family members, and the date of activation of card 12. New daily per capita nutritional consumption averages are then calculated by computer 40. By way of communication link 43 and read-write unit 14, computer 40 transmits the new daily per capita nutritional consumption averages to smart card 12 for storage in smart card's memory to be used and updated at the next purchase. Computer 40 transmits the same new daily per capita nutritional averages through link 51 to printer 18 which prints the new averages. Consumer withdraws his/her smart card 12 from read write unit 14 and receives the printed dietary consumption report in the form of a table. This way consumer's personalized smart card 12 always contains the latest statistical (historical) averages of dietary nutrient consumption which is updated at the next food or drink purchase, may it be at a supermarket, food market, or a restaurant.

Dietary nutritional data on all types, sizes, and brands of foods and drinks sold in supermarkets and product identification codes for the same are entered into computer 40 intended for use in a supermarket or a food store at the time computer 40 is programmed to carry-out the requirements of this invention. The data may be tabulated against manufacturers' names or UPC or EAN numbers, and includes name of the producer, name of the product, product size in ounces or grams or number of servings, and nutrient contents per unit weight such as calories per ounce and sodium in mg per serving, protein in g per ounce, and so on.

Figures 3, 4:
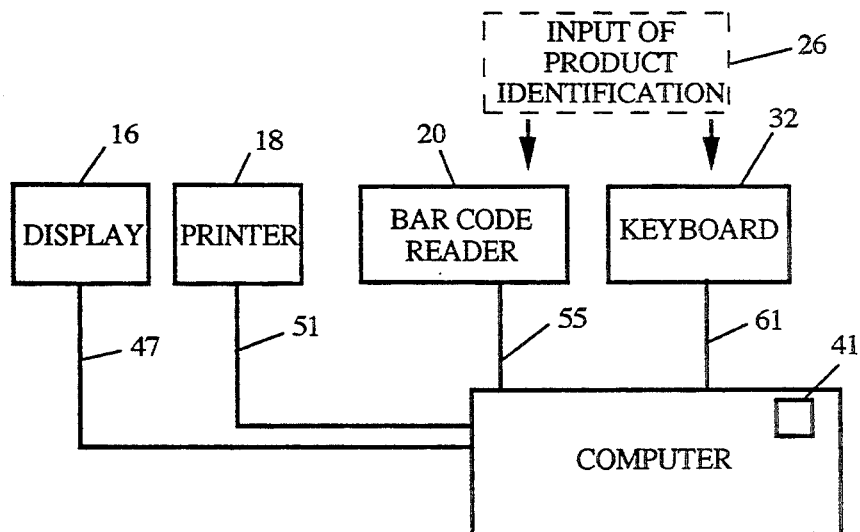
FIG. 3 is a second example of a personalized dietary consumption report.
FIG. 4 is a block diagram of the nutritional consumption data monitoring system in accordance with a second embodiment of the invention which does not allow personalization of the nutritional data.

By way of example only and not by way of limitation, two different formats for displaying and/or printing the dietary consumption report prepared for a fictitious family, John Doe Fit and family, and a fictitious person, Jane Doe, are shown in FIGS. 2 and 3 respectively.

Referring now to FIG. 2, computer 40 may be programmed to generate a dietary consumption report showing average daily per capita consumption of nutrients of type of concern in diet control such as calories, % of calories from fat, cholesterol in mg, etc. as shown in left hand column 71 of table 70 in FIG. 2. The average daily per capita nutritional consumptions in table 70 are collated in two columns 73 and 75 for the time periods "to date" and "last 30 days" respectively to conveniently show dietary consumption trends. Total family members 76, card activation date 78, and report date 79 are identified above the top left corner of table 70. A knowledge of total number of family members 76 is necessary for computation by computer 40 of per capita consumption of nutrients identified in column 71. A knowledge of card activation date 78 is needed for computation by computer 40 of average daily amounts of nutritions consumed per person as listed under column 73. To compute the new average amounts of nutrients consumed per person per day for the period between card activation date and the current transaction date, computer 40 is programmed to take the amounts written under column 73 stored in memory of smart card 12, multiply them with the elapsed number of days between card activation date 78 from memory of card 12 and the current transaction date, add the last purchase amounts per person written under column 77 from memory of card 12, and divide the totals by the elapsed number of days between card activation date 78 and current date.

Average daily amounts of nutrients consumed per person within the last 30 days written under column 75 in memory of card 12 are updated by computer 40 by multiplying the average values listed under column 75 with 30 minus the elapsed number of days between report date 79 in memory of card 12 and the current date, and adding the last purchase per capita amounts listed under volume 77 in memory of card 12, and dividing the totals by 30 days. Column 75 is updated by computer 40 by erasing old numbers from column 75 stored in memory of smart card 12 and replacing it with the new numbers just calculated, computer 40 erases the old last purchase amounts per person under column 77 in memory of card 12 and enters the current purchase amounts per person as the new "last purchase" amounts per person under column 77 in memory of card 12. Computer then writes the new report date in location 79 in the memory of smart card 12, thus completes updating of the memory of smart card 12.

Company or organization, issuing the personalized smart card, has the freedom to program individual preferences into the personalized smart card. For example, recommended daily consumption amounts of certain nutrients, or recommended daily consumption maximums, may be written in the memory of a smart card, and these would then be listed alongside the daily per capita consumption averages for nutrients printed in the dietary consumption report for comparison. Cholesterol, sugar, and sodium are among those nutrients that may be limited to a maximum daily average intake by a physician for some persons. Such recommended values and limits may not be the same for everyone, thus individualized limits may preferably be written into the smart card's memory by the card issuer as requested by the consumer. There is shown in FIG. 3, an example of a dietary consumption report showing recommended daily limits of some nutrients for a fictitious person, Jane Doe.

Referring now to FIG. 3 for a second example of a dietary consumption report, computer 40 may be programmed to generate a dietary consumption report showing average daily per capita consumption of nutrients of type of concern in diet control such as calories, calories from fat, cholesterol in mg, etc. as well as recommended daily amounts of all or some of these nutrients may be shown in the dietary consumption report for comparison. Recommended daily amounts, as shown in FIG. 3 under column 81, are individual preferences requested by consumers and are used as comparison purposes. Consumers' preferences may reflect recommendations of their dietitians or physicians. The average per capita dietary nutrient consumptions in table 80 are collated in two columns 83 and 85 as described above for the dietary consumption report of FIG. 2. The numbers under columns 83 and 85 may also be expressed as percent of the recommended numbers under column 81.

Nutritional data categories other than those shown in column 71 in FIGS. 2 and 3 may also be included in the dietary consumption reports. Additionally, average daily nutritional consumptions may be reported as percentages of ideal values or as percentages of ideal values as determined by the consumers' age, height, etc. It will be understood that the foregoing general description is exemplary and explanatory of the invention but is not restrictive thereof.

In an alternative embodiment of the invention shown in block diagram in FIG. 4 the system in its simplest form is shown. Here the system consists of means such as a computer 40 for storing and processing nutritional information of the type of concern in diet control, means such as a real time clock 41 for maintaining current date record, means such as a product code entry terminal 32 or a bar code reader 20 for inputting product identification information, and means such as a printer 18 for printing nutritional information, and optionally means 16 for displaying such information. Nutritional data of the type of concern in diet control on all types of foods and drinks sold at food markets, supermarkets, restaurants, and the like are pre-stored in computer 40. Nutritional data on the foods and drinks being purchased at a check-out counter are extracted from the memory of computer 40 each time computer 40 receives a signal from bar code reader 20 or from manual data entry terminal 32 identifying the food or drink being purchased. Nutritional data on all food and drink items purchased at the check-out counter and extracted from the memory of computer 40 are sorted and collated in a temporary memory zone of computer 40, and at the completion of the purchase transaction, the nutritional data is printed out as a summary report such as the report shown in FIG. 5. This simple form of the system is capable of informing the consumer of the nutritional content of his/her purchase at the check-out counter, but does not allow historical nutritional data to be conveniently developed, summarized, and stored in a personalized smart card. To monitor progress of his/her diet control efforts, consumer in this simplest form of the invention must collect printed food store check-out reports, chronologically sort them, and analyze the nutritional intake trends personally. While this method of diet control may be less convenient and open to errors, it is also less costly since the costs associated with purchase and distribution of smart cards to consumers, installation of card reader writer devices at food and drink selling stores and restaurants would be eliminated.

Advantageously, since many of the food markets and supermarkets already have in their check out systems, bar code readers, terminals for manual entry of product codes, printers that print receipts, and a computer with memory that stores product related information such as cost, size and manufacturer, smart card read write units and smart cards forming part of the present invention can be retrofitted to existing electronic check-out counter systems in a known manner through a communications link. The software used in the supermarket computers may be modified to include dietary nutrients information on foods and drinks, and may be modified within the skill in the art to enable the computer to carryout computations of the kind required by the present invention, thus eliminating the need for a separate computer dedicated for use in the diet control operations.

Thus, there is disclosed herein a system and a method for recording and monitoring of individualized nutritional consumption information of the type of concern in diet control. It will be seen that the objects set forth above, among those made apparent from the preceding description, are efficiently attained and, since certain changes may be made in the above construction without departing from the scope of the invention, it is intended that all matter contained in the above description or shown in the accompanying drawing figures shall be interpreted as illustrative only and not restrictive thereof.

It is also understood that objects and advantages of the invention am set forth in part herein and in part will be obvious herefrom, or maybe learned by practice with the invention, the same being realized and attained by means of the instrumentalities and combinations pointed out in the appended claims.

I claim:

1. A method for electronically recording and monitoring of nutritional information of the type of concern in diet control when foods and drinks are purchased by a consumer at a location where food and drinks are sold for human consumption by a consumer, said method including providing computer means with memory for storing nutritional and product identification information on foods and drinks available at said location and enabling said computer means to process said nutritional information and said product identification information;

providing means for transmitting product identification information of said foods and drinks when being purchased at said location;

providing real time clock means connected to said computer means for maintaining current date record and for determining duration of said recording and monitoring activity for the purpose of creating daily averages of nutritional consumption by said consumer;

providing card reader writer means connected to said computer means through a known communication link;

providing at least one consumer smart card enabled to communicate with said computer means through said reader writer means, wherein said consumer smart card has memory to store said consumer's personalized information and to store current and historical nutritional consumption data received from said computer means, wherein said current nutritional consumption data include nutritional contents of said foods and drinks purchased in the latest purchase transaction, and said historical nutritional consumption data include averages of daily nutrition consumption by said consumer averaged over selected periods of time;

providing printer means connected to said computer means by a known communication link for printing a dietary report generated by said computer means, said dietary report containing personalized nutritional consumption information including said current and historical nutritional consumption data for said consumer;

enabling said computer means to communicate with said smart card through said reader writer means, and to communicate with said printer means, said display means, and with product identification transmission means;

said consumer, prior to start of said current purchase transaction, inserting said smart card into said reader writer means, thereby informing said computer means of readiness of said smart card to provide and receive information;

transmitting product identification information on said foods and drinks being purchased by said consumer to said computer means;

maintaining a current date record and determining duration of said recording and monitoring activity by a real time clock;

said computer means creating a list of totals of said nutritions in said foods and drinks purchased;

said computer means operated to create new daily averages of nutrition consumption by said consumer by using historical daily nutrition consumption data stored in said smart card memory, totals of said nutritions from last purchase stored in said smart card memory and elapsed number of days since said smart card has been activated;

said computer means through said card reader writer means erasing said smart card memory containing historical daily averages of nutrition consumption by said consumer and said list of totals of said nutrition from last purchase;

said computer means through said reader writer means writing into said smart card memory new daily averages of nutrition consumption by said consumer and said current list of totals of said nutrition in said foods and drinks purchased;

said printer means providing to said consumer said dietary report generated by said computer means, said dietary report containing said new daily averages of nutrition consumption by said consumer and said current list of totals of said nutrition in said foods and drinks purchased;

said consumer then retrieving said smart card from said reader writer, and storing said smart card until the next food and/or drink purchase transaction.

2. A method as defined in claim 1, including providing at least a part of said memory of smart card in the form of electronically erasable programmable memory used to store data on daily averages of nutrition consumption by said consumer and said current list of totals of said nutrition in said foods and drinks purchased at said location.

3. A method as defined in claim 2, including updating said data on daily averages of nutrition consumption by said consumer and said current list of totals of said nutrition in said foods and drinks purchased at said location by operation of said computer means through said reader writer means, each time said smart card is used at said location.

4. A method as defined in claim 3, including providing and operating display means for displaying nutritional contents of said foods and drinks as foods and drinks are purchased at said location.

5. A method as defined in claim 4, including programming said smart card to provide to said computer means nutrition consumption limits preferred by said consumer as a reference to be printed in said dietary report.

* * * * *